(12) United States Patent
Hirshberg (10) Patent No.: US 9,931,478 B2
(45) Date of Patent: Apr. 3, 2018

(54) NEEDLES SYSTEM

(71) Applicant: David Hirshberg, Haifa (IL)

(72) Inventor: David Hirshberg, Haifa (IL)

( * ) Notice: Subject to any disclaimer, the term of this patent is extended or adjusted under 35 U.S.C. 154(b) by 899 days.

(21) Appl. No.: 14/326,537

(22) Filed: Jul. 9, 2014

(65) Prior Publication Data
US 2014/0323837 A1    Oct. 30, 2014

Related U.S. Application Data (63) Continuation-in-part of application No. 13/426,684, filed on Mar. 22, 2012, now Pat. No. 9,409,006.

(60) Provisional application No. 61/473,779, filed on Apr. 10, 2011.

(51) Int. Cl.
| | |
|---|---|
| *A61M 5/32* | (2006.01) |
| *A61M 5/50* | (2006.01) |
| *A61B 5/15* | (2006.01) |
| *A61B 5/145* | (2006.01) |
| *A61N 1/36* | (2006.01) |
| *A61B 17/3205* | (2006.01) |
| *A61M 5/20* | (2006.01) |
| *A61M 37/00* | (2006.01) |
| *A61N 1/05* | (2006.01) |
| *A61B 17/00* | (2006.01) |

(52) U.S. Cl.
CPC .......... *A61M 5/3297* (2013.01); *A61B 5/145* (2013.01); *A61B 5/14532* (2013.01); *A61B 5/15* (2013.01); *A61B 17/32053* (2013.01); *A61M 5/20* (2013.01); *A61M 5/5086* (2013.01); *A61M 37/0015* (2013.01); *A61N 1/3605* (2013.01); *A61B 2017/00017* (2013.01); *A61B 2017/00345* (2013.01); *A61B 2017/00752* (2013.01); *A61B 2017/00761* (2013.01); *A61M 2005/206* (2013.01); *A61M 2037/003* (2013.01); *A61M 2037/0023* (2013.01); *A61M 2037/0053* (2013.01); *A61M 2037/0061* (2013.01); *A61N 1/0502* (2013.01)

(58) Field of Classification Search
CPC .......... A61B 5/0492; A61B 2562/0285; A61B 2017/00345; A61B 5/14514; B81B 2201/055
See application file for complete search history.

(56) References Cited

U.S. PATENT DOCUMENTS

| | | | |
|---|---|---|---|
| 2007/0106143 A1* | 5/2007 | Flaherty | A61B 5/04001 600/373 |
| 2012/0158100 A1* | 6/2012 | Schomacker | A61B 18/1477 607/101 |

* cited by examiner

*Primary Examiner* — Matthew F Desanto (57) ABSTRACT

A needle system for penetrating to or passing thought an object or an organ comprising a semiconductor die, one or more needles, wherein the needles slide over the plane of the die, one or more actuators that move the needles relative to the die plane, and one or more actuator drivers controlled by a controller wherein the controller instruct the needle to penetrate into or to pass through and/or retract from the object or organ. The needle system is used for drug delivery or blood extraction or blood analysis or glucose measurements or blood measurements or nerve system stimulus treatment or hair removal or skin lesions removal.

20 Claims, 6 Drawing Sheets

NEEDLES SYSTEM

RELATED APPLICATION/S

This application is a continuation-in-part (CIP) of U.S. patent application Ser. No. 13/426,684 filed Mar. 22, 2012, which claims priority under 35 U.S.C. § 119(e) of U.S. provisional patent application 61/473,779 filed Apr. 10, 2011. The contents of the above documents are incorporated by reference as if fully set forth herein.

FIELD AND BACKGROUND OF THE INVENTION

The present invention, in some embodiments thereof, relates to needles that penetrate objects or organs, and more particularly, but not exclusively, to a needles that is used for medical treatments for humans.

Needles are thin objects, optionally hallow, with sharp tip in its end to allow penetration into or passage through an object or organ. Needles have many usages. It is used in sewing, in crafting for making small holes, in research, especially in biology, and in medicine. In medicine needles are used to inject fluid into or extract fluid from the body as well as in other treatments such as stimulating treatments, like acupuncture, or for monitoring treatment, like brain activity probing.

On of the most popular needle is a hypodermic needle that is penetrating the skin. In some applications the needle is injecting fluid to or extracting from the intercellular fluids and in other case extracting blood from or injection drugs to a blood vassal.

Typically, today, hypodermic needle is made of stainless-steel and the diameter of the needle is between 0.2 mm, i.e., 200 micron, to 5 mm. In recent years some needles in the thin diameter range are made also from other materials, such as silicon. These needles are produced using semiconductors manufacturing processes and fabrication facilities.

SUMMARY OF THE INVENTION

According to an aspect of some embodiments of the present invention there is provided needle system that penetrates objects or organs, in general and more particularly, but not exclusively, needle system that is used for medical treatments for humans.

According to an aspect of some embodiments of the present invention there is provided a needle system for penetrating to or passing thought an object or an organ comprising:
(a) a semiconductor die;
(b) one or more needles, wherein the needles slide over the plane of the die;
(c) one or more actuators that move the needles relative to the die plane; and
(d) one or more actuator drivers controlled by a controller; wherein the controller instruct the needle to penetrate into or to pass through and/or retract from the object or organ.

According to some embodiments of the invention, the needles are inserted none perpendicularly to anchoring the needle system into the object or organ.

According to some embodiments of the invention, the needle system comprises plurality of semiconductor dies.

According to some embodiments of the invention, first semiconductor dies is assembled perpendicular to second semiconductor dies and the second semiconductor dies comprises vias which the needles are passing through those vias.

According to some embodiments of the invention, the needle movement mechanism comprises a ratchet mechanism to lock the needle movement between movements' steps.

According to some embodiments of the invention, the actuators are electromagnetic or electrostatic or piezoelectric actuators.

According to some embodiments of the invention, the needle has mechanical support to hold the needle and to allow sliding only to a desired direction.

According to some embodiments of the invention, the needle system has friction reduction mechanism to reduce the needle friction during sliding over the die.

According to some embodiments of the invention, the needle is hollow.

According to some embodiments of the invention, the needle system is used for drug delivery or blood extraction or blood analysis or glucose measurements or blood measurements or nerve system stimulus treatment or hair removal or skin lesions removal.

According to an aspect of some embodiments of the present invention there is provided a method for penetrating to or passing thought an object or an organ using a needle system comprising the steps of:
a) attaching to the object or organ a needle system comprising one or more needles, wherein the needles system comprising needles that slide over the plane of a die, and one or more actuators move the needle relative to the die plane, and one or more actuator drivers controlling the actuators using a controller; and
b) controlling the actuators to move the needle to penetrate into or to pass through or retract from the object or organ.

According to some embodiments of the invention, one or more needles are inserted none perpendicularly to anchoring the needle system into the object or organ.

According to some embodiments of the invention, the needle system comprises plurality of semiconductor dies.

According to some embodiments of the invention, first semiconductor dies is assembled perpendicular to second semiconductor dies and the second semiconductor dies comprises vias which the needles are passing through those vias.

According to some embodiments of the invention, the needle movement mechanism comprises a ratchet mechanism to lock the needle movement between movements' steps.

According to some embodiments of the invention, the actuators are electromagnetic or electrostatic or piezoelectric actuators.

According to some embodiments of the invention, the needle has mechanical support to hold the needle and to allow sliding only to a desired direction.

According to some embodiments of the invention, the needle system has friction reduction mechanism to reduce the needle friction during sliding over the die.

According to some embodiments of the invention, the needle is hollow.

According to some embodiments of the invention, the needle system is used for drug delivery or blood extraction or blood analysis or glucose measurements or blood measurements or nerve system stimulus treatment or hair removal or skin lesions removal.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, some hardware for performing selected tasks according to embodiments of the invention, if not explicitly specified, could be implemented as a chip or a circuit. As software, selected tasks according to embodiments of the invention could be implemented as a plurality of software instructions being executed by a computer or controller using any suitable operating system. In an exemplary embodiment of the invention, one or more tasks according to exemplary embodiments of method and/or system as described herein are performed by a processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1a is a top view of the needle system in close, i.e., initial, position;

FIG. 1b is a cross section of the needle system across line AA designated in FIG. 1a;

FIG. 1c is a top view of the needle system in fully open position;

DESCRIPTION OF SPECIFIC EMBODIMENTS OF THE INVENTION

The present invention, in some embodiments thereof, relates to needles that penetrate objects or organs, and more particularly, but not exclusively, to needles that are used for medical treatments for humans.

The current technology of needle systems does not couple between the needle fabrication and the needle mechanical subsystem that is responsible for the insertion and retraction of the needles to the target object or organ. Currently there are two prominent ways of controlling penetration and retraction of the needle: manually or spring activated. In manual activation, the doctor, nurse or patient sticks and retracts the needle with his hand. Such an operation has it limitations both in accuracy and in the speed of operation. Spring operated activation uses the mechanical energy stored in a string to inject or retract the needle. This operation is fast but requires excessive strength requirements from the needle. In many cases, the logic behind high speed insertion is to reduce the pain associated with needle insertion and it is based on the fact that if the insertion is fast enough, the nerve system will not be as fast to respond. This is true only if the needle does not strike directly a nerve sensor, i.e., pacinian corpuscle. Spring activation can not control the depth of penetration and only a full penetration design by the spring system activation can be achieved. Usually spring activation needle system is responsible only for the insertion or the retraction and the complement operation is done manually.

The current invention is teaching integrating fabrication of a needle with the fabrication of a mechanical subsystem, which is responsible for the insertion and the retraction of the needle into and from the target object, into a single die using semiconductor fabrication techniques. Both the needle and the mechanical subsystem are fabricated using semiconductor fabrication techniques allowing achieving, among other things, very thin needles. Much thinner then stainless-steel needles can be achieved. Another advantage is the ability to manufacture, with a low cost, array of needles that has an advantage over a single needle system in many applications, as will be described later on. Having semiconductor micro mechanical (MEMS) system capability enables very flexible and accurate mechanical operation. For example, the needle may penetrate the object using very small movement steps, with a step resolution of several micro-meters. The penetration speed and force can be preciously controlled over time using digital micro controller that is optionally integrated into the needle system, optionally, on the same die. The ability of very slow insertion of the needle enables novel not currently in use scheme to avoid pain. If the needle is inserted very slowly, the pressure that the nerve system feels is less than the pain threshold hence the patient does not feel the needle insertion. In addition, such scheme that is not possible in current needle system technologies enables reduction in the requirement for strength of the needle and enable thinner and more reliable needle. In addition, the ability to stop the penetration in any depth, potentially with the aid of other monitoring signals in the loop, open the doors for many new feature such as (1) penetration to the exact depth in the tissue, i.e., the epidermis, the dermis, or the hypodermis; (2) avoid sticking a blood vassal; (3) targeting to a blood vassal; (4) avoid or targeting nerve sensors; (4) avoid or targeting hair papillae; (5) avoid or targeting sweat glades.

As used herein, the term "die" means a rectangle chip fractured from a semiconductor wafer and manufactured in semiconductor foundry by semiconductor fabrication processes. The term "chip" and the term "die" are alternately used in this application and essentially mean the same. Note that the die is not necessarily made of semiconductor material rather is manufactured using facilities that are usually is used to fabricated semiconductors dies.

As used herein, the term "substrate" means the material layer the wafer is made of which all additional layers and structure are fabricated on top of it.

Optionally, the needle system comprises an array of needles enable activation of some of the needles in this array selectively based on the needle location.

Before explaining at least one embodiment of the invention in detail, it is to be understood that the invention is not necessarily limited in its application to the details of construction, fabrication techniques and the arrangement of the components and/or methods set forth in the following description and/or illustrated in the drawings and/or the Examples. The invention is capable of other embodiments or of being practiced or carried out in various ways.

Figure 1A:
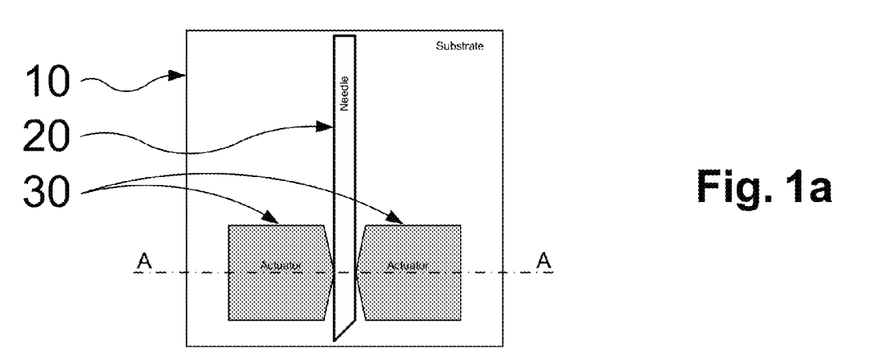
FIG. 1a-FIG. 1c are illustrations of an exemplary embodiment of simplified construction and operation of the present invention needle system.
Figure 1B:
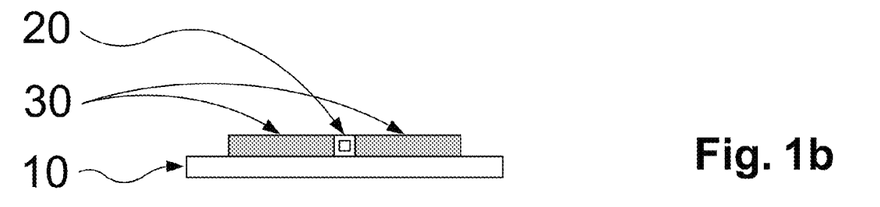
Figure 1C:
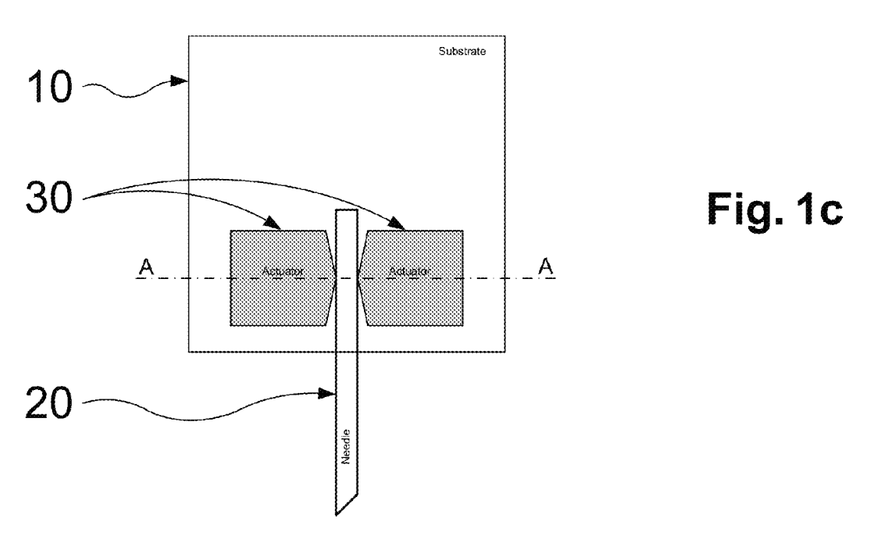

For purposes of better understanding some embodiments of the present invention, as illustrated in FIGS. 1-7 of the drawings, reference is first made to FIG. 1. FIGS. 1a-1c illustrate a principle simplified construction and operation of the present invention. FIG. 1a present a top view of the needle system in close, i.e., initial, position. FIG. 1b present a cross section view of the needle system across line AA designated in FIG. 1a. FIG. 1c presents the top view of the needle system in fully open position. The simplified needle system comprises a die substrate 10, a needle 20 and an actuator 30. Needle 20 is fabricated as a floating element over substrate 10 so it can be slide over substrate 10. Needle 20 is contacted to actuator 30 that can slide the needle over the substrate. In specific the needle 20 can exceed the die edge and get out of the chip boundary and penetrate a target object if it is attached to the chip edge. Needle 20 can be produced from silicon, silicon oxide, or any other materials that can be grown or printed on substrate 10 using semiconductor fabrication processes. To achieve a floating needle structure the needle is fabricated on top of a thin temporary layer (for example silicon oxide) that is etched away after needle fabrication. To reduce the friction between substrate 10 and needle 30, a small dimples array optionally imprinted. The needle system and actuators 20 are build such that a full accurate control of needle insertion is possible. Both the length of insertion and the velocity of insertion are adjustable. It is also possible to retract the needle back to its initial position inside chip substrate 10. Retraction time and retraction velocity is also fully controlled.

As used herein, the term "actuator" means an element or a component or a circuit or a complex of elements that configured to mechanically move or displaced another element, e.g., a needle.

Figure 2:
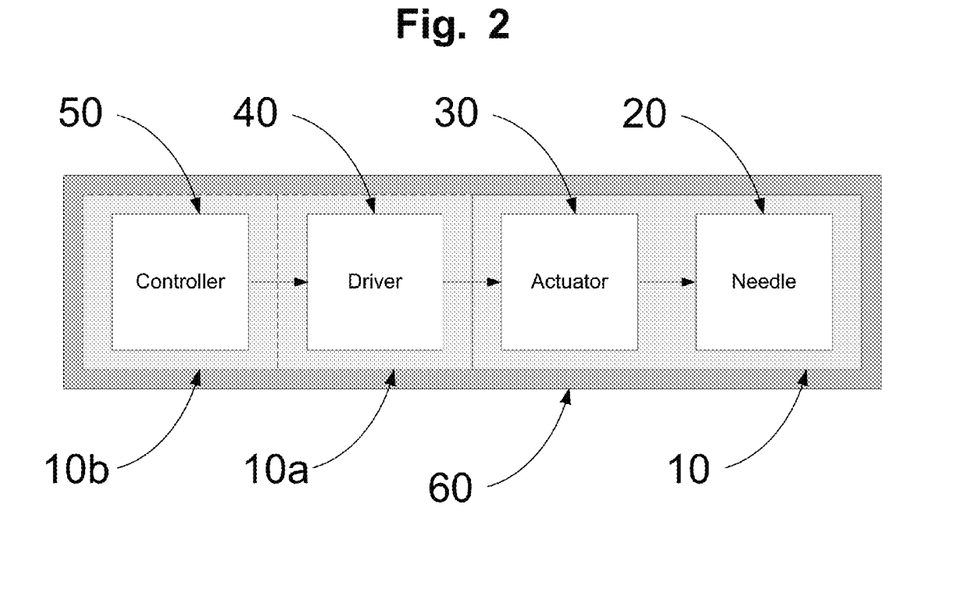
FIG. 2 is a block diagram of a minimal simplified needle system in accordance with the present invention.

Reference is now made to FIG. 2. FIG. 2 illustrates a block diagram of a minimal simplified needle system in accordance with the present invention. Needle 20 is a needle as illustrated in FIG. 1. Actuator 30 is in contact with Needle 20 and can move needle 20 between initial position and fully open position, as illustrated in FIG. 1. Actuator 30 moves needle 20 according to signal from an actuator driver 40.

Actuator driver 40 drives current or voltage signals to activate actuator 30. Optionally, driver 40 drives multiple signals to activate actuator 30. Optionally, driver 40 drives complex signaling like sine waves, pulse waves or any complex time function signals to activate actuator 30. Optionally, driver 40 drives digital signaling to activate actuator 30. Typically driver 40 is implemented using analog electronic elements such as transistors. As used herein, the term "actuator driver" means an element or a component or a circuit or a complex of elements that configured to electrically signaling and controlling the actuator operation.

The full needle system is controlled by a controller 50. Controller 50 instructs the driver to generate the appropriate signals to move needle 20. Controller 50 determines system level operation parameters, such as, when the insertion of the needle will starts?, for how long in time and in what velocity needle will penetrate?, what will be the depth of penetration?, for how long the needle will be inside the object?, how long it will take to retract the needle?, etc. Typically controller 50 is implemented as a digital micro controller with a processor, memories and peripherals and it is running embedded software on it.

Needle 20 and actuator 30 are fabricated on a single semiconductor die 10 as illustrated in FIG. 1. Driver 40 is optionally fabricated on the same die, i.e., die 10, or alternatively on independent die, die 10a. Controller 50 is optionally fabricated on the same die, i.e., die 10, or alternatively on independent die, die 10b. When needle 20, actuator 30, driver 40 and controller 50 are integrated on the same die we have a single die system. Optionally, die 10a and die 10b are implemented as a single die and the full needle system is implemented as a two die system. Such a configuration has several advantages and is specifically illustrated and describe later on. Optionally, needle system has external package 60. External package 60 size and shape depends on the actual application of the needle system and the organ it is aimed to penetrate to. For example, an adhesive patch package may be used to attach the needle system to the skin. In a different application the package may contains straps to tight the needle system to the organ. To fulfill sterilization requirements external package 60 may be sealed with a dedicated membrane to enable needles to get out from package 60.

Figure 3:
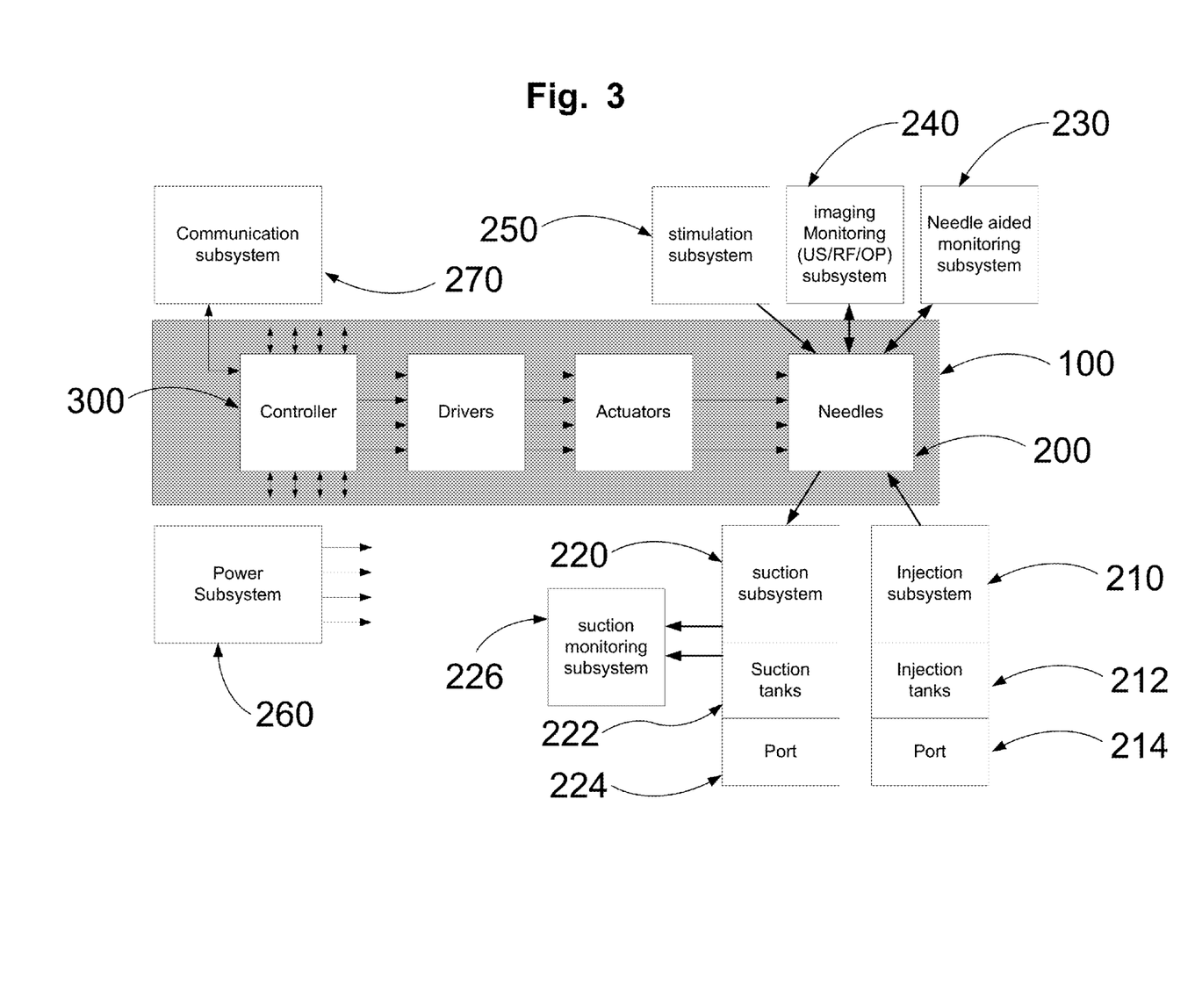
FIG. 3 is a block diagram of a more complete needle system that implement more advanced applications in accordance with the present invention.

Reference is now made to FIG. 3. FIG. 3 illustrates a block diagram of a more complete needle system that implements more advanced applications in accordance with the present invention. The core of the system is needle subsystem 100 that comprising from one or more needles 200 moved by one or more actuators driven by one or more actuators drivers controlled by one or more controllers. Needles 200 optionally attached to injection subsystem 210 that is designed to inject fluid materials though the needle to the target organ or object. The injection materials are stored in one or more injection tanks 212. Injection tanks 212 are optionally externally refilled using injection port 214.

Needles 200 optionally attached to a suction subsystem 220. Suction subsystem 220 is designed to suck or extract fluid materials from the target organ or object. The extracted materials are stored in one or more suction tanks 222. The material in suction tanks 222 are optionally transferred externally using injection port 224. Suction material optionally directly transferred to build in monitoring system 226. Optionally, suction monitoring system 226 monitor the suctioned material stored in suction tanks 222. Monitoring may be a concentration of a specific molecule in the extracted fluid, e.g., glucose concentration in blood, or any other property of the sampled suctioned material.

Needles 200 optionally attached to a needle aided monitoring subsystem 230. Needle aided monitoring subsystem 230 is designed to measure parameters of the needle current state or needle tip surroundings or the target organ/object using needles 200. Since typically needles 200 are electrically conductive driving electric signal to the needle may revile some desirable properties. For example measuring the electric resistivity between two adjacent needles that are inserted together can revile the type of tissue the needles are in. measuring the resistive force the needle is facing during the insertion stage can also help in reviling the tissue the needle tip is reaching. More sophisticated measurements involving injection and detection of ultrasonic (US), radio frequencies (RF) or optical signals (OP) or any other type of energy injection through the needles is optionally provided. The aim of the energy transmission and energy reflection in needle aided monitoring subsystem is to measure parameters relevant to the actual needle tip in its specific position.

Needles 200 optionally attached to an imaging monitoring subsystem 240. Imaging monitoring subsystem 240 is designed to provide the controller a 2D or 3D image of the target organ/object. The image can be constructed using injection and detection of ultrasonic (US), radio frequencies (RF) or optical signals (OP) or any other type of energy that can provide the necessary information. In case needles 200 are constructed as an array they are well fit to be used as the source, the energy guides and the sensors for the image monitoring. Optionally, imaging monitoring subsystem 240 is using none attached to needle elements such as transmitters and detectors build-in in the system to create an image independently from needles 200. Imaging monitoring subsystem 240 is connected to controller 300. The image information is used by controller 300 to select the right needle to perform the task optimally and to set the correct or optimal depth for penetration for each active needle. The image information may be also dynamically processed to analyze the actual results of the treatment and to decide its dynamics and its completion.

Needles 200 optionally attached to a stimulation subsystem 250. stimulation subsystem 240 is designed to transfer energy through the needle to specific target areas in the target organ/object. Stimuli is ultrasonic (US), radio frequencies (RF), optical signals (OP) or any other type of energy that can effect the target organ. Optionally, stimuli are given to destroy object in the organ. For example stimuli may be electric signal to create or prevent pains in the nerve system. Stimuli can also be a signal that destroy nerve sensor or hair papilla or sweat glade.

The needle system contains power subsystem 260 that provide energy for operation of all other subsystems. Power subsystem 260 optionally contains battery, optionally rechargeable battery. Power subsystem 260 optionally contains charger, optionally wireless charger. Power subsystem 260 optionally contains power port for external power source. Power subsystem 260 optionally contains energy convertor that takes energy from the environment to power the system or charge power subsystem 260 batteries.

The needle system contains communication subsystem 270 that enables communication with other adjacent systems. Preferable communication media is wireless but optionally wired communication is used. Communication subsystem 270 is connected to controller 300. Communication subsystem 270 is optionally connected to the patient smart phone. Controller 300 may get instructions from outside or provide data to the patient and/or the patient health information system, optionally contained processing and storage elements in the cloud. Communication subsystem 270 optionally contains indicators, displays, buttons and/or keyboards to locally interact with the patient or, in general, the needle system operator.

The Needle Movement System

The following section with its accompanying figures is describing in greater details the design, fabrication and mechanical aspects of the needle actuation and movement. There are four elements in this discussion that affect each other: (1) the step motor or step actuation and step movement of the needle; (2) the locking mechanism or ratchet mechanism that restrict the direction of movement and locks the needle between movement steps which is optionally needed to combat resistive forces from the target object to the needle movement that try to force the needle back to its previous position; (3) the sliding support elements that direct and enable the movement of the needle only in the desired directions, and hold the needle against shear forces etc; and last, (4) the friction between the needle and the support elements and die or substrate, that in general, resist the movement of the needle.

Figure 4:
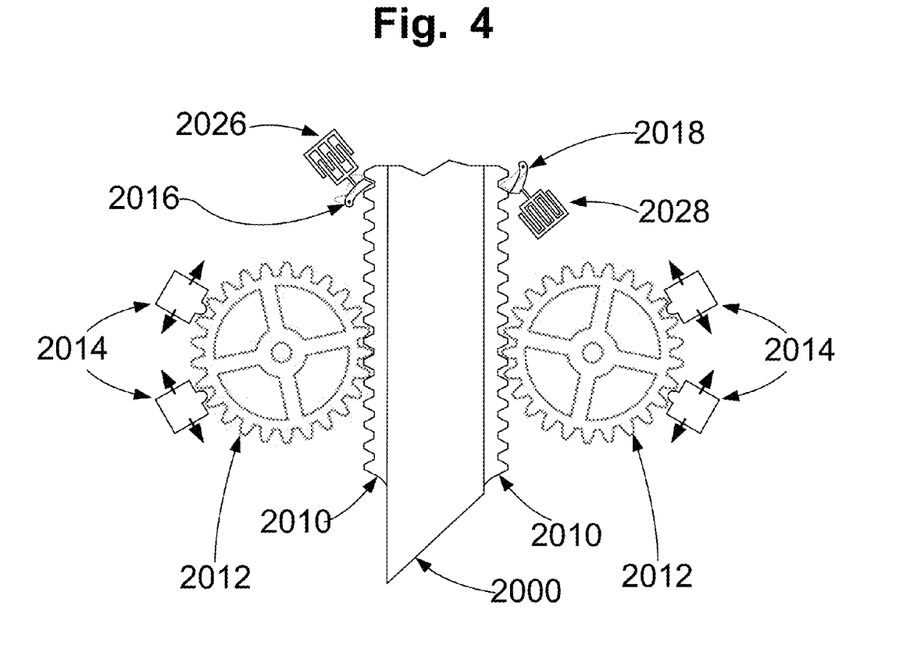
FIG. 4 is a is top view of a needle movement subsystem with force transmission and ratchet mechanism imprinted on the die plane in accordance with a preferred embodiment of the invention.

Reference is made now to FIG. 4. FIG. 4 illustrates an example for needle movement subsystem with force transmission and ratchet mechanism. The figure is top view of the structure imprinted on the die plane. Teeth bars 2010 are fabricated in the sides of needle 2000. The linear movement of the needle is generated by the rotation of teeth wheels 2012. Rotating a teeth wheel on MEMS is well known in the art and many actuators and MEMS engines architectures have been developed and can be used to convert actuation cycles to rotation. Variable transmission power techniques may also used to achieve the required delivered force to needle 2000. Alternatively, actuators can directly drive teeth bars 2010 and for example, create a move of one tooth displacement in each actuation step. In the figure, a four actuators 2014 are presented each two actuators 2014 drive a single teeth wheel 2012. Note that teeth wheels 2012 are used as power transitions that both collect and sum the power from actuators 2014 and convert the direction of power from diagonal to parallel to the needle axis. To provide mufti-activation cycle of the actuator without teeth wheel 2012 rotating back, a staggered activation of each actuator 2014 pair attached to the same teeth wheels 2012 is used. In this case, carful design of the teeth geometry allow actuator 2014 to perform its backward movement while the other actuators 2014 perform it forward movement and vise versa. In this way, the forward movement will rotate the wheel while the backward movement will not rotate the wheel. Alternatively, actuator 2014 movement cycle is slightly elliptical allowing movement in one direction to rotate teeth wheel 2012 and to disconnect from the teeth wheel 2012 hence not rotate the wheel in the other direction. In addition to the needle movement subsystem, a ratchet mechanism based on the existence of teeth bars 2010 is presented in the figure. The ratchet mechanism may be one way ratchet that ensures no backwards movement during penetration or ensure no forward movement during withdrawal of the needle. Optionally or alternatively, two-way ratchet can be used as illustrated in FIG. 4.

A ratchet tooth 2016 prevents penetration movement and a ratchet tooth 2018 prevents withdrawal movement. Both ratchet teeth 2016 and 2018 can be active or inactive. In the figure, ratchet tooth 2016 is active and ratchet tooth 2018 is inactive so the needle in this case can not penetrate but can retract. Actuators 2026 control ratchet tooth 2016 and actuators 2028 control ratchet tooth 2018. Actuators 2026 and 2028 push the teeth to activate the ratchet operation and pull the ratchet teeth to deactivate the ratchet operation.

Figure 5:
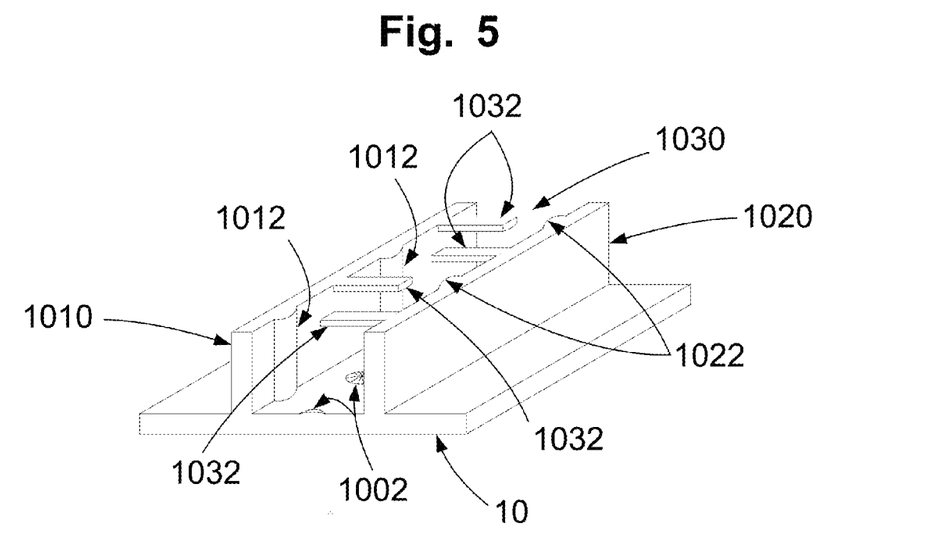
FIG. 5 is an isometric view of needle sliding support and friction reduction subsystem imprinted on the die plane in accordance with a preferred embodiment of the invention, for clarity the needle itself is not shown and only the geometric concepts, not in scale, are shown.

Reference is made now to FIG. 5. FIG. 5 illustrate an example for needle sliding support and friction reduction subsystem. The figure is isometric view of the imprinted structure but for clarity the needle itself that is imprinted together with sliding support and friction reduction subsystem is not shown. For clarity, the figure is not in scale and the geometric concepts are shown. The bottom part of the sliding support is the die 10. Die 10 is optionally coated with other layers. To support the sliding, left wall 1010 and right wall 1020 are fabricated. The needle itself is fabricated inside the needle cavity 1030. To reduce the friction of the needle with needle cavity 1030 boundaries, the surface of cavity 1030 is spotted with smooth rounded bumps. The floor of needle cavity 1030 is covered with rounded bumps 1002. Left wall 1010 is covered with bumps 1012. Fabrication constrains limit bumps 1012 to be rounded only in the axis parallel to die 10 plane rather than be rounded in both dimensions. Optionally, two dimensions rounded bump are used. Similarly, right wall 1020 is covered with bumps 1022. To support the needle from the top sides, rods 1032 are fabricate. Rods 1032 surfaces that face needle cavity 1030 are rounded as well to reduce friction. Alternatively, the top support of needle cavity 1030 is fabricated by another die that assemble as the cover package of the needle system.

Friction and wear are well known issue in MEMS moving parts and there are many ways known in the art to reduce friction in MEMS devices. Before naming a few it is to be understood that since the needle in most applications, as described hereinafter, is inserting and retracting the object only once and in slow motion the friction and wear is less of a problem in the present invention in comparison to other MEMS device. Having said that, the other known methods to reduce friction includes smoothing the sliding surfaces with different type of etching, coating the surfaces with different type of materials, lubricating the sliding surfaces with liquids or gases. Using micro balls bearing is another option. Another class of methods is to keep the sliding surface apart using electrostatic or electromagnetic forces. In this case the friction may be used as a ratchet mechanism and the needle is forced to detach from the sliding support only when the step actuation is active, i.e., only when the needle moves.

Many types of MEMS actuators can be used to move or drive the needle. The most common ones are electro-static, electro-magnetic and piezoelectric. Piezoelectric electric actuation is being a good choice since there are well known ways to implement a step motor with locking (ratchet) mechanism as illustrated in FIG. 6.

Figure 6:
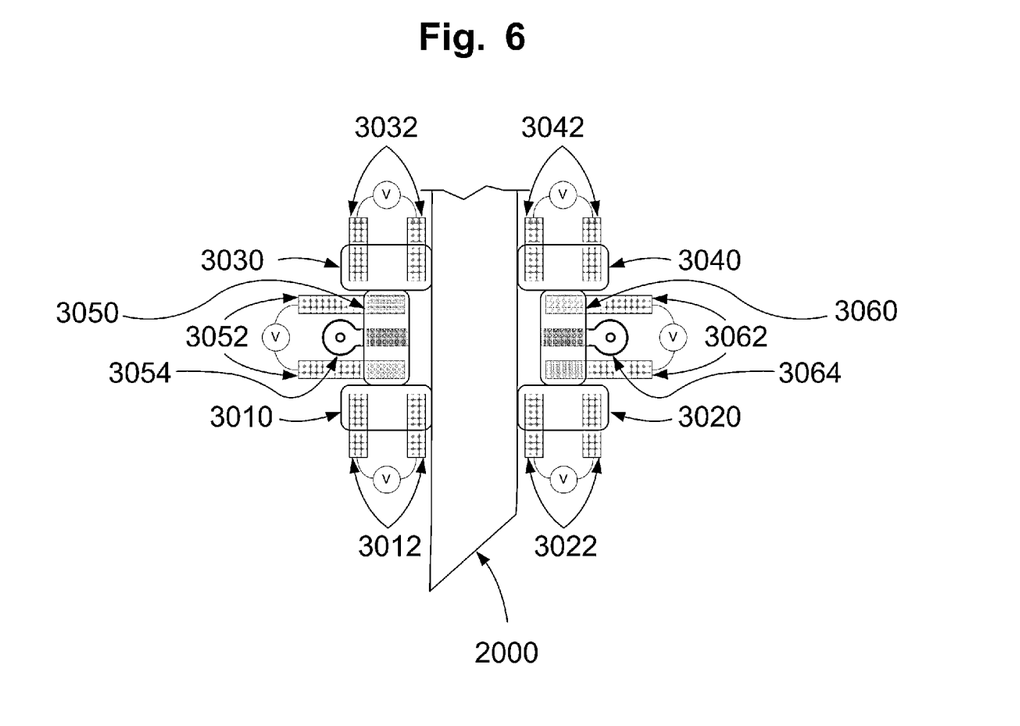
FIG. 6 is a top view of needle actuation and ratchet subsystem using piezoelectric actuators imprinted on the die plane in accordance with a preferred embodiment of the invention, for clarity only the relevant elements are shown.

Reference now made to FIG. 6. FIG. 6 illustrates an example of needle actuation and ratchet subsystem using piezoelectric actuators. The figure is a top view of the imprinted structure and for clarity only the relevant elements are shown. In rest position needle 2000 is locked by four piezoelectric crystals 3010, 3020, 3030 and 3040. Each piezoelectric crystal 3010, 3020, 3030 and 3040 have a pair of electrodes 3012, 3022, 3032 and 3042 located on the crystals edges. Applying positive voltage, i.e. voltage in the same polarity as the piezoelectric crystal, to electrodes 3012, 3022, 3032 and 3042 expend the crystals hence increase the gripping force on needle 2000 and increase the locking of the needle to its position. Applying negative voltage to electrodes 3012, 3022, 3032 and 3042 contract the crystals hence free the needle to move. The full step motor structure contains additional two piezoelectric crystals 3050, 3060 each one of them is located in opposite side with respect to needle 2000. Electrodes 3052 are connected to piezoelectric crystal 3050 and electrodes 3062 are connected to piezoelectric crystal 3060. Piezoelectric crystal 3050 is mechanically attached to the die using anchor 3054. Piezoelectric crystal 3060 is mechanically attached to the die using anchor 3064. During needle insertion motion, i.e., motion downwards in the figure, the needle system controller initiates a specific sequence of instructions as describe herein. In the first step, crystals 3030 and 3040 expand and crystals 3010 and 3020 contract so that the needle is hold only by crystals 3030 and 3040. Next, crystals 3050 and 3050 contract and since crystals 3050 and 3060 are anchored to the die needle 2000 move downwards. Next, crystals 3010 and 3020 contract and hold needle 2000. Next, crystals 3030 and 3040 contract therefore they release their grip from needle 2000. The next step is expanding of crystals 3050 and 3060 that cause needle 2000 to further move downwards. This cycle can continue as long as the controller wants to insert needle 2000 further into the target organ or object. To retract needle 2000 a similar sequence is applied but now the controller contracts crystals 3050 and 3060 when crystals 3010 and 3020 hold needle 2000 and expands crystals 3050 and 3060 when crystals 3030 and 3040 hold needle 2000. Other structures of piezoelectric configuration with different structure of crystals and electrodes may be used as well.

System Integration and Packaging

Figure 7:
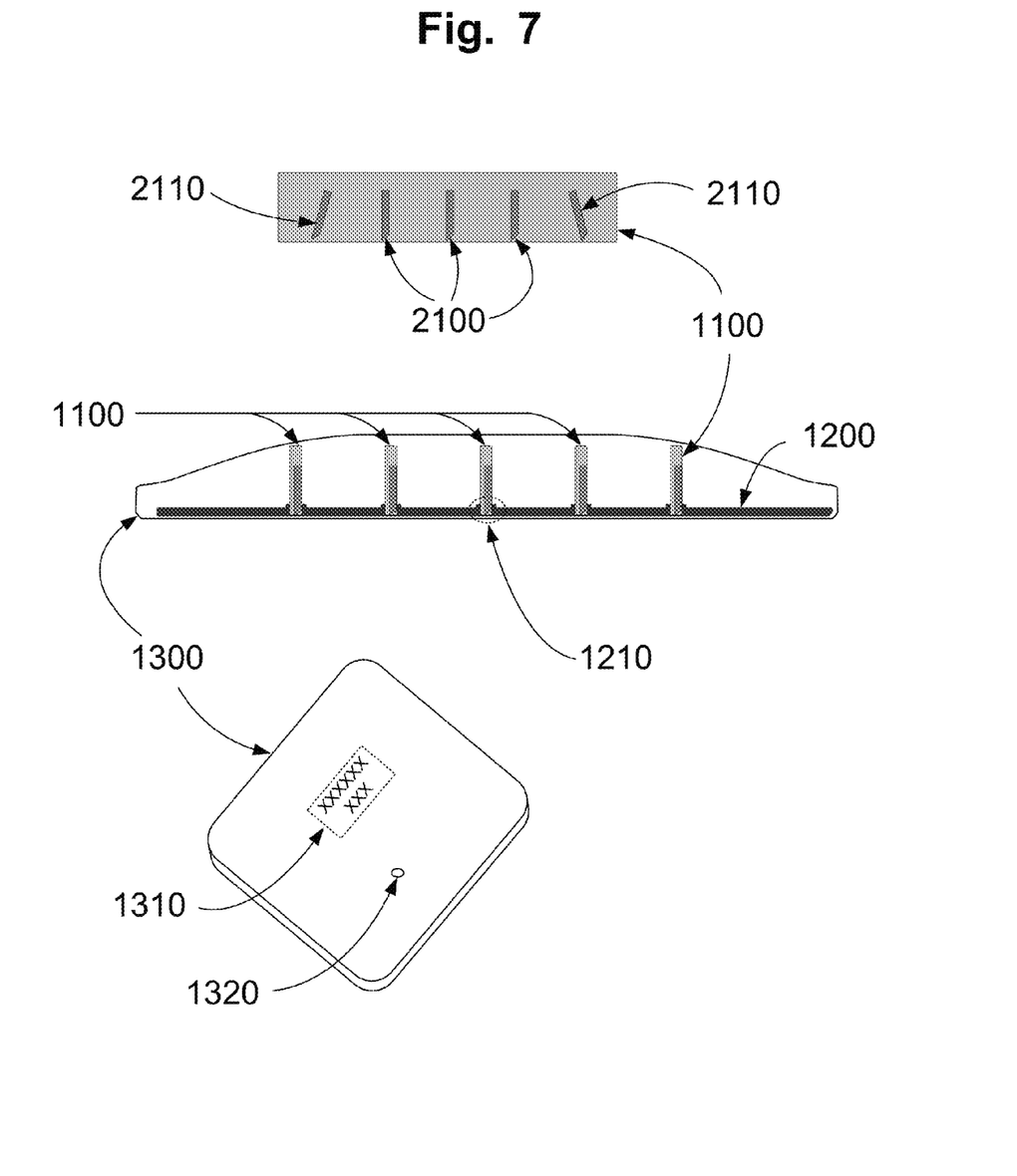
FIG. 7 is a full needle system assembly view in accordance with a preferred embodiment of the invention.

Reference now made to FIG. 7. FIG. 7 illustrates an example of full needle system assembly according to the present invention. The figure contains three views of the system and its components: in the top, a side view of MEMS needle chip 1100 in accordance with the present invention; in the middle, a cross section of adhesive patch package 1300 contains several MEMS needle chips 1100 and one system chip 1200; and in the bottom view, an isometric view of adhesive patch package 1300. MEMS needle chip 1100 contains five needles. The two needles in the die edges, needles 2110, are tilted outwards to provide additional anchoring effect to adhesive patch package 1300 when inserted into the target organ. The other three needles 2100 are vertically placed and are inserted perpendicular into the target organ. Adhesive patch package 1300 is a sealed package with adhesive material at its bottom side that glue the package to skin of the target organ. Inside package 1300 there is a system chip 1200 contains standard digital electronic elements comprising the controller and the actuator drivers. System chip 1200 contains connection areas 1210 that include vias to enable passage of the needles through system chip 1200, electronic contacts that transfer signals between system chip 1200 and MEMS needle chips 1100 and mechanical support structure to hold the MEMS needle chips 1100 in vertical position. Adhesive patch package 1300 optionally includes a label 1310 to identify the patch and some UI elements, such as an indicator 1320 that indicates, for example, that the needle system complete its task.

As used herein, the term "via" means a hole passing through the die that enable objects, such as the needle, to pass through it.

Needle System Applications

The present invention needle system incurs several general advantages:
1) Painless accurate slow penetration;
2) Painless slow retraction;
3) Infection immunity—the slow retraction solves a major problem of needle treatment which is infection, when a needle retracts at once there is an open tunnel for bacteria and viruses to penetrate the body, those infections may be very dangers. In the present invention, the slow retraction gives the skin tissue the time to repair itself and close the opened tunnel as the needle retracts. When the needle is fully retracted, the skin is already closed and the possibilities for infections to penetrate the skin are illuminated.

4) System integration—Manufacturing the full system on a single die or several dies that are tightly coupled and assembled in the fab, allows additional integration with other monitoring and control capabilities. The needle can precisely reach the right place. The right place may be the boundaries between tissues, like the boundary between the epidermis and the subcutaneous fat tissue or between the subcutaneous fat tissue and the muscles, or avoiding or targeting organs in the tissues like blood vessels, nerve system components, sweat system components, hair components or other organs. Using monitoring capabilities in the needle itself like electrical resistance measurements or other measurements using sensors like ultrasound, RF or optical sensors can provide the information for accurate targeting of the needles.

The following four advantages and capabilities open the door for a vast range of medical applications that can be implemented using the present invention as describe hereinafter.

In an exemplary embodiment of the invention, drug delivery system is disclosed. In this application, a drug tank or a cocktail of drugs in several separate tanks are integrated into a needle system implemented in accordance with the present invention. On a preset timing, a needle is penetrating the skin and the drug is injected with the appropriate dose. The system can be used repeatedly to provide drug delivery for longer periods, e.g., one week. The needle system can be used to deliver several drugs in a single system with accurate time correlation between the deliveries of each drug. The needle system optionally comprises several needles and each drug is delivered using different needle. For example, a first drug is delivered by injection into the epidermis and the needle will penetrate less then 1 mm and a second drug, made from bigger molecules, need to be injected to the intercellular fluids, so the needle will penetrate the skin until it pass the epidermis and reach a "wet tissue". Further more, if third drug is needed to be injected directly into a blood vassal, a third needle will be targeted to bring the needle tip into the interior of a blood vassal. Additionally or alternatively, a measurement subsystem is integrated to set the dose dynamically based on a measured parameter.

In an exemplary embodiment of the invention, a device for painless and harmless blood extraction for performing blood tests is disclosed. The device is strapped to a regular area of blood taking, i.e. an area where a blood vain is close to the skin, e.g., above the wrist or above the elbow. The system has monitoring or imaging capability and it scan the covered skin area, identify a target blood vain and move the appropriate needle, implemented according to the present invention, to the exact penetration in order to extract the blood from the selected blood vain. Blood will be taken out from a port integrated into the device. Additionally or alternatively, the blood measurement is done on the device and the results are transmitted to the health care information system.

In an exemplary embodiment of the invention, a glucose measurement device is provided. The glucose measurement device include an array of needle in accordance with the present invention, each needle is associated with a glucose measurement subsystem. Each time the controller selects to make a measurement, it instructs a needle to penetrate the skin to a proper depth and a glucose measurement is taken. The measurement can be transmitted via wireless link to the patient smart phone or patient monitoring device or to the health care information system. One patch with plurality of needle may be used for taking glucose measurements for several days. The patient does not feel nor know when the measurement is taken. Measurements can be taken in predefined manner, e.g., morning, noun, evening, or in dynamic manner. For example, if there is a high level reading the measurements sampling rate may increase.

In an exemplary embodiment of the invention, a fat removal device is implemented. The fat removal device is a patch that is placed in areas of excessive subcutaneous fat tissue. The patch contains an array of needles in accordance with the present invention. The needles penetrate the skin and reach the subcutaneous fat tissue. When the needles reach to the target tissue the suction subsystem sucks a portion of the fats or portion of the fat cells to a tank on the device. When the suction ends the patient remove the patch from skin and through it away.

In an exemplary embodiment of the invention, a nerve system treatment device is disclosed. The device contains an array of micro needle that are used to stimulate the human nerve system. The inspiration behind this device is similar to acupuncture treatment, i.e., to stimulate the nerve system for relaxing or therapeutic uses. More accurate targeting of nerve sensors and electric stimuli through the needles can be achieved using needle system implemented in accordance with the present invention.

In an exemplary embodiment of the invention, a skin lesions remover device is disclosed. The device is putted on the lesion, scan it and analyze it. The device contains an array of needle in accordance to the present invention. The device, using the needles, optionally analyzes the lesion. Analyzing contains measure of the properties of the lesion like its strength and depth into the benign tissue. After analysis the device kill the lesion by mechanically insertion and retracting the needles into the lesion or alternatively or optionally by electrical burning using the needles or optionally or alternatively by chemically or biologically materials injection into the lesion. The patch/device is placed on the lesion for several days. Optionally the device measure the effectiveness of the treatment and when the device removed the lesion is totally removed and healthy skin is grown instead.

In an exemplary embodiment of the invention, hair removal device is disclosed. The device is putted on hairy skin area. The device contains an array of needle in accordance to the present invention. The device scans the locations of the hair papillae and targets a needle to each hair papilla. When the needle reaches the papilla it burns it either by electric signal or by chemical injection.

The following needle system is very precise and versatile. Due to the tightly integration with other capability offered by the semiconductor industry the present invention can be used for non medical applications as well. Those can be for sawing fabrics, precise fabrication of micro elements, R&D tools, lab equipments, etc.

It is expected that during the life of a patent maturing from this application many relevant applications will be developed and the scope of the implementation is intended to include all such new technologies a priori.

The terms "comprises", "comprising", "includes", "including", "having" and their conjugates mean "including but not limited to".

The term "consisting of means "including and limited to".

As used herein, the singular form "a", "an" and "the" include plural references unless the context clearly dictates otherwise. For example, the term "an element" or "at least one element" may include a plurality of elements, including mixtures thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A semiconductor micro mechanical needle system for penetrating to or passing thought an object or an organ comprising:
   one or more semiconductor dies, and
   one or more actuator drivers controlled by a controller,
   at least one of the semiconductor dies is a needle semiconductor die comprises:
   (a) substrate having a top surface parallel to a plane of the needle semiconductor die;
   (b) one or more needles, wherein the needles are fabricated above the substrate on top of a temporary layer that is etched away after needles fabrication, the needles are floating over the substrate and the needles are configured to slide over the substrate in parallel to the plane of the needle semiconductor die; and
   (c) one or more actuators that are connected to the substrate and the needles and move the needles relative to the substrate,
   wherein the one or more actuator drivers activate the one or more actuators, and the controller is capable to instructs the needles to penetrate into or to pass through and/or retract from said object or organ, and
   wherein the system is configured to electrically transfer signals between the one or more semiconductor dies, one or more actuators, one or more actuator drivers and the controller.

2. The needle system of claim 1, wherein said needle system comprises a plurality of [identical needle] semiconductor dies.

3. The needle system of claim 2, further comprising vias that enable the one or more needles of the needle semiconductor die to pass through the semiconductor system.

4. The needle system of claim 1, wherein one or more said needles are configured to be inserted at an angle to said object or organ in order to anchor said needle system into said object or organ.

5. The needle system of claim 1, wherein the needle movement mechanism comprises a ratchet mechanism to restrict the direction of movement and lock said needle movement between movements' steps.

6. The needle system of claim 1, wherein said actuators are electromagnetic or electrostatic or piezoelectric actuators.

7. The needle system of claim 1, wherein said needle has mechanical support to hold the needle and to allow sliding only to a desired direction.

8. The needle system of claim 1, wherein said needle system has friction reduction mechanism to reduce said needle friction during sliding over said die.

9. The needle system of claim 1, wherein said needle is hollow.

10. The needle system of claim 1, wherein said needle system is used for drug delivery or blood extraction or blood analysis or glucose measurements or blood measurements or nerve system stimulus treatment or hair removal or skin lesions removal.

11. A method for penetrating to or passing through an object or an organ using a semiconductor micro mechanical needle system comprising one or more semiconductor dies, one or more actuator drivers controlled by a controller, wherein at least one of the semiconductor dies is a needle semiconductor die comprising:
   (a) a substrate having a top surface parallel to a plane of the needle semiconductor die;
   (b) one or more needles, wherein the needles are fabricated above the substrate on top of a temporary layer that is etched away after needles fabrication, the needles are floating over the substrate and the needles are configured to slide over the substrate in parallel to the plane of the needle semiconductor die;
   (c) one or more actuators that are connected to the substrate and the needles and move the needles relative to the substrate,
   the method comprises the steps of:
   attaching to an object or organ the semiconductor micro mechanical needle system; and
   controlling the actuators to move the needle to penetrate into or to pass through or retract from said object or organ by using the controller to electrically control the one or more semiconductor dies, one or more actuators and one or more actuator drivers.

12. The method of claim 11, wherein said needle system comprises a plurality needle semiconductor dies.

13. The method of claim 12, wherein the needles of said needle semiconductor dies are passing through vias of other one or more semiconductor die.

14. The method of claim 11, wherein one or more said needles are inserted at an angle to said object or organ in order to anchor said needle system into said object or organ.

15. The method of claim 11, wherein the needle movement mechanism comprises a ratchet mechanism to restrict the direction of movement and lock said needle movement between movements' steps.

16. The method of claim 11, wherein said actuators are electromagnetic or electrostatic or piezoelectric actuators.

17. The method of claim 11, wherein said needle has mechanical support to hold the needle and to allow sliding only to a desired direction.

18. The method of claim 11, wherein said needle system has friction reduction mechanism to reduce said needle friction during sliding over said die.

19. The method of claim 11, wherein said needle is hollow.

20. The method of claim 11, wherein said method is used for drug delivery or blood extraction or blood analysis or glucose measurements or blood measurements or nerve system stimulus treatment or hair removal or skin lesions removal.

* * * * *